(12) United States Patent
Ebinger et al.

(10) Patent No.: US 12,742,743 B2
(45) Date of Patent: Sep. 22, 2026

(54) DEVICE AND METHOD FOR DETECTING A CORROSIVE AMBIENT ATMOSPHERE IN A PROTECTIVE HOUSING

(71) Applicant: Turck Holding GmbH, Halver (DE)

(72) Inventors: Klaus Ebinger, Kempen (DE); Michael Bauer-Wesely, Grünhain-Beierfeld (DE); Christian Leonhardt, Chemnitz (DE); Robert Schulze, Chemnitz (DE)

(73) Assignee: Turck Holding GmbH, Halver (DE)

( * ) Notice: Subject to any disclaimer, the term of this patent is extended or adjusted under 35 U.S.C. 154(b) by 297 days.

(21) Appl. No.: 18/618,070

(22) Filed: Mar. 27, 2024

(65) Prior Publication Data

US 2024/0328976 A1 Oct. 3, 2024

(30) Foreign Application Priority Data

Apr. 3, 2023 (DE) .................... 10 2023 108 449.6

(51) Int. Cl.
*G01N 25/66* (2006.01)
*G01N 17/02* (2006.01)
*G01N 33/00* (2006.01)

(52) U.S. Cl.
CPC ............. *G01N 25/66* (2013.01); *G01N 17/02* (2013.01); *G01N 33/0027* (2013.01)

(58) Field of Classification Search
CPC ........ G01N 25/56; G01N 25/66; G01N 17/02; G01N 33/0027
See application file for complete search history.

(56) References Cited

U.S. PATENT DOCUMENTS

2015/0268152 A1 9/2015 Friedersdorf et al.
2018/0149579 A1 5/2018 Brookhart et al.
(Continued)

FOREIGN PATENT DOCUMENTS

DE 10 2018 128 063 A1 5/2020
EP 3 787 165 A1 3/2021
(Continued)

OTHER PUBLICATIONS

Machine Translation of JP-2013170923-A (Year: 2013).*
(Continued)

*Primary Examiner* — Nguyen Q. Ha
(74) *Attorney, Agent, or Firm* — Pearl Cohen Patentanwälte PartGmbB; Michael McCandlish

(57) ABSTRACT

A device determines an intensity of a corrosive ambient atmosphere in a protective housing. The device includes at least two internal sensors designed to detect changes over time in different ambient parameters inside the protective housing, and to generate sensor signals reflecting the changes over time in the different ambient parameters; an evaluation device designed to receive the sensor signals and to evaluate the sensor signals in correlation with one another in order to determine the intensity of the corrosive ambient atmosphere on basis of deviations of the sensor signals, or of a parameter correlated with the sensor signals, from a reference value or reference value range, taking into account a time duration and/or frequency of the deviations; and an output device designed to generate an output signal reflecting the determined intensity of the corrosive ambient atmosphere.

14 Claims, 2 Drawing Sheets

(56) References Cited

U.S. PATENT DOCUMENTS

| | | | |
|---|---|---|---|
| 2020/0333272 | A1 | 10/2020 | Wang et al. |
| 2022/0057279 | A1 | 2/2022 | Kumar et al. |

FOREIGN PATENT DOCUMENTS

| | | | | |
|---|---|---|---|---|
| JP | 2012189356 | A | | 10/2012 |
| JP | 2013170923 | A | * | 9/2013 |
| TW | I787971 | B | | 12/2022 |

OTHER PUBLICATIONS

Extended European Search report issued in EP 24 167 294.8, which is a counterpart hereof, mailed on Aug. 13, 2024, and English machine translation thereof.

German Search Report issued in DE 10 2023 108 449.6, to which this application claims priority, mailed Jul. 21, 2023, with english language machine translation thereof.

* cited by examiner

DEVICE AND METHOD FOR DETECTING A CORROSIVE AMBIENT ATMOSPHERE IN A PROTECTIVE HOUSING

CROSS REFERENCE TO RELATED APPLICATIONS

This application claims priority to German patent application 10 2023 108 449.6 filed on Apr. 3, 2023, which is hereby incorporated by reference in its entirety.

TECHNICAL FIELD

The present disclosure relates to a device for detecting a corrosive ambient atmosphere in a protective housing, optionally a switch cabinet, and a method for operating a device of this type.

BACKGROUND

It is known from the prior art for corrosion to be detected on the basis of changes in the material characteristics of a workpiece, optionally using optical, electrical and/or electrochemical methods. This is a suitable approach in applications in which corrosion is unavoidable and represents a normal wear behavior, for example of a component. The disadvantage of this approach is that the corrosion has already started at the location defined by the measurement setup. In addition, no findings are available regarding the extent of the corrosion at other locations, for example on other components installed in a protective housing. The known measuring methods are in some instances highly complex and often cannot be implemented in switch cabinets.

In the technical domain, in particular related to switching and industrial plant technology, corrosion is a phenomenon which very frequently has unwanted consequences. These include, on one hand, a change in the material characteristics of the I/O components installed in a switch cabinet or—in extreme cases—total destruction of one of these I/O components. Particularly due to the current trend toward decentralized automation, switch cabinets and protective housings are preferably installed close to machinery and, as a result, are exposed to a considerable extent to hazardous and corrosive ambient conditions.

For corrosion detection, determining the impact of corrosion inside a protective housing using an optical sensor which detects wavelength changes of UV radiation reflected in the protective housing is known from US 2022/0057279 A1.

For corrosion protection, sensors having sacrificial anodes made from base materials which are typically arranged at an exposed location in order to actively corrode in an existing corrosive ambient atmosphere are further known from the prior art. A procedure of this type in turn enables only retrospective corrosion detection, i.e. after corrosion has already taken place, which can be identified, for example, on the basis of electrical characteristics, in particular electrical conductivity, of the sacrificial anode that have changed as a result of corrosion.

In the domain of protective housings or switch cabinets, complex air conditioning, ventilation and/or filter systems are known which are configured to establish constant and, as far as possible, non-corrosive ambient conditions inside the switch cabinet. However, a procedure of this type is economically viable only in an environment with highly expensive instruments, since the components necessary for this purpose, such as e.g. a gas-tight switch cabinet, filter systems, etc., are typically technically sophisticated and, in particular, require constant maintenance and monitoring.

It would be desirable to detect the degree of incipient corrosion in a timely manner or to predict it before it occurs. Particularly in switch cabinets and/or similar types of protective housings, a corrosive atmosphere can in some cases infiltrate with corrosion-related failure of the protective function, which can result within a short time in destruction of the installed I/O components.

SUMMARY

In this context, and as a non-limiting example, one object of the present disclosure can be to indicate a device for detecting a corrosive ambient atmosphere in a protective housing, optionally a switch cabinet, and a method for operating a device of this type, wherein corrosion can be determined in a timely manner, optionally before it occurs.

The object is achieved accordingly by a device for detecting a corrosive ambient atmosphere in a protective housing, optionally a switch cabinet, comprising:

- at least two internal sensors designed to detect the changes over time in different ambient parameters, optionally an air temperature and/or a component temperature, an air humidity and/or a gas concentration, inside the protective housing, and to generate a sensor signal reflecting the respective change over time in the respective ambient parameter;
- an evaluation device configured to receive the sensor signals reflecting the respective changes over time in the different ambient parameters and to evaluate them in correlation with one another in order to determine the intensity of the corrosive ambient atmosphere on the basis of deviations of the sensor signals, or of a parameter correlated with the sensor signals, from a reference value or reference value range, taking into account of a time duration and/or frequency of the deviations; and
- an output device configured to generate an output signal reflecting the determined intensity of the corrosive ambient atmosphere.

The at least two internal sensors are arranged, optionally, inside the protective housing, optionally in the switch cabinet.

The disclosure is based, inter alia, on the measurement of relevant ambient parameters, such as air temperature and/or component temperature, relative or absolute air humidity, gas concentration, optionally of corrosive gases, inside the protective housing or the switch cabinet. It is, in an example, proposed to consider not only limit values, but also the temporal aspect of changing ambient conditions which is reflected accordingly in the changes over time in the measured ambient parameters. In this way, the time period, optionally, indicating how long a detected contamination lasts and how frequently the contamination occurs is taken into account in the evaluation of the sensor signals in order to obtain meaningful information relating to the occurrence of an atmosphere conducive to corrosion and in order to reliably determine the intensity of the corrosive ambient atmosphere.

Corrosion-related damage, optionally to components installed in the protective housing, such as e.g. I/O components of a switch cabinet, can thus ideally be avoided. The intensity of the corrosive ambient atmosphere can be output via the output device, for example a display screen, LED display or other output device, so that, optionally, a warning can be output to the user, for example in the form of traffic light warning signals, if a corrosive ambient atmosphere with increased intensity has been identified. The output can further be implemented via a data connection to a network or a cloud service. An electronic message, email or short message (SMS) can be sent, or a warning message can be output at a superordinate control level.

In other examples of applications, a recommended action can be output depending on the determined intensity of the corrosive ambient atmosphere. Alternatively or additionally, actuators are activatable for the performance of corresponding immediate actions so that a control dependent on the determined intensity of the corrosive ambient atmosphere is implemented. According to different designs, for example, a heating, a cooling, an air conditioning system, a suction device and/or a filter system is/are connected to the evaluation device in such a way that said evaluation device is activatable according to the output signal and can be activated, optionally, depending on the determined intensity of the corrosive ambient atmosphere.

Particularly in the industrial plant technology domain, undetected corrosion often results in a restriction of the function or—in extreme cases—an unscheduled total failure resulting in the shutdown of a complete plant or machine. Damage caused by corrosion can also have a negative impact on safety parameters (FUSI, Ex) of a plant, particularly in the case of switch cabinets. It is therefore advantageous to detect the risk of occurrence of corrosion in a timely manner in order to be able to instigate countermeasures as appropriate.

In examples, the intensity of the corrosive ambient atmosphere can be calculated or determined in a local evaluation device, optionally a processor or microchip, or by means of a cloud application which is connected, for example, via an intranet or the Internet. In examples, the signals, optionally sensor signals and/or output signals, are transmitted by wired or wireless means, for example via optical waveguides WLAN or the like.

In examples, the device can be designed, optionally, as a retrofit kit for installation in existing switch cabinets.

In one design, the evaluation device further includes a trained model, optionally a deep learning model, which is trained in a learning phase to classify the intensity of the corrosive ambient atmosphere on the basis of the changes over time in different ambient parameters. The use of artificial intelligence for determining the intensity of the corrosive ambient atmosphere is particularly advantageous because it is not necessary to specify the intensity as a function of material parameters, ambient parameters, and/or other environmental parameters. Instead, the model can be trained using empirically determined learning data to classify the intensity of the corrosive ambient atmosphere on the basis of the sensor signals.

The, optionally supervised, learning or training of the model takes place in the operation of test setups exposed to given ambient conditions which are constantly monitored and measured by the internal sensors. These setups are preferably not monitored until the onset of corrosion in order to obtain learning data which are suitable for training the model.

In a further example, the evaluation device is designed to determine the intensity of the corrosive ambient atmosphere, taking into account a corrosion behavior of a corroding testpiece empirically determined in advance, particularly in an initialization phase and/or learning phase already mentioned above. The testpiece typically includes a base material of which the corrosivity compared with other materials installed in the protective housing is quantitatively known and/or can be determined.

In order to be able to identify a change in corrosive ambient conditions, it is expedient in some instances to measure the extent of the corrosivity during the initialization. This can be done, for example, using the above-mentioned testpiece. The testpiece consists of a base material which changes its electrical characteristics, optionally its electrical conductivity, over a defined time period of the initialization. The change over time in an electrical characteristic, optionally electrical conductivity, is measured in this defined time period. The testpiece is installed at an exposed location in the protective housing or switch cabinet. Following the initial measurement or initialization, the testpiece is no longer required and can therefore also be removed. However, the initialization can be repeated at any time if ambient conditions change.

Any corrosive ambient atmosphere can be determined as an initial state on the basis of data obtained during the initialization. A further measurement of the aforementioned ambient parameters, such as e.g. temperature, humidity and gas concentration of corrosive gases, is performed during operation. The obtained values and changes over time in the ambient parameters can be compared with those of the initial state in order to derive courses of action therefrom and issue them to the user. Optionally, it can thus be established whether, with regard to corrosion, constant, improved and/or deteriorated ambient conditions are present.

In examples, the initialization phase serves to train the model, optionally the deep learning model, on which the evaluation is based; in this respect, it is provided to use data generated during the initialization described above, optionally relating to changes in the material characteristics of the testpiece as a result of corrosion, as learning data for the model that is to be trained. In examples, the learning data of the model thus contain, optionally, information relating to the time duration and frequency of deviations of the ambient parameters from a predefined or predefinable reference value or reference value range during the initialization. The correlation with the sensor signals on which the determination of the intensity of the corrosive ambient atmosphere is based is therefore predefined or learned in the case of models trained in this way.

In a further example, at least one of the internal sensors can be configured as an air humidity sensor and at least one further of the internal sensors can be configured as a temperature sensor. The evaluation device can be designed to determine the intensity of the corrosive ambient atmosphere taking into account a dew point calculated on the basis of the sensor signals of the air humidity sensor and of the temperature sensor.

In other words, the dew point is determined as at least one of the parameters which is correlated with the measured ambient parameters and forms the basis for determining the intensity of the corrosive ambient atmosphere. Particularly in the case where the temperature on a component, optionally an I/O component, or on a housing wall or switch cabinet wall approximates or falls below the dew point, condensation conducive to corrosion is to be expected.

The internal sensors are preferably installed at defined locations in the protective housing or switch cabinet in order to enable a comprehensive representation of the corrosive ambient conditions. The internal sensors are particularly preferably arranged such that extremes of the temperature distribution inside the protective housing or switch cabinet, such as cold spots or hotspots, are measurable. In this way, condensation, optionally, developing in the protective housing or switch cabinet can be detected in a timely manner.

In examples having a plurality of temperature sensors, these sensors can be arranged such that a substantial measured temperature difference between the corresponding measuring points is to be expected.

In a further example, the temperature sensor can be configured to measure the temperature of a cold spot inside the protective housing, wherein the temperature sensor defines an essentially isolated measuring point at the cold spot or is designed as a surface temperature sensor. Particularly in the case of switch cabinets, cold spots can often be found in the area of an external wall close to any air conditioning and/or cooling that is present, so that it is appropriate to measure the temperatures prevailing locally there in order to be able to detect condensation conducive to corrosion in a timely manner.

In a further example, the temperature sensor is designed as an optical sensor, optionally as an IR sensor. In possible applications, an IR sensor is directed, for example, at the coldest point on an external wall of a cabinet or at an area of a ventilation or cooling of a switch cabinet in order to provide temperature-dependent sensor signals.

In a further example, at least one of the internal sensors of the device for detecting the corrosive ambient atmosphere can be configured to measure a gas concentration of a corrosive gas, particular a halide ion concentration, a chloride concentration and/or hydrogen sulfide concentration, inside the protective housing. The existence of corrosive gases containing halogenated compounds, optionally with chloride dissolved in water, can be caused optionally by a location close to the sea. Gases containing hydrogen sulfide can occur, for example, at locations close to chemical plants.

In possible examples, one of the internal sensors can be designed as a door sensor and can be configured to determine, as an ambient parameter, whether a door of the protective housing is open or closed. An open door is generally conducive to the development of corrosion.

In a further example, the evaluation device is designed to receive local climate data and/or geographical location data which contain information dependent on the geographical location of the protective housing, and to take the data into account in determining the intensity of the corrosive ambient atmosphere. To do this, the evaluation device can be designed, for example, to receive weather data from a local weather station or corresponding external sensors.

The geographical location of the installation can be reliably obtained, for example, by means of GPS (Global Positioning System) or a similar satellite-based navigation system. Particularly in conjunction with weather data relating to external temperature, wind speed, etc., local correlations with location-dependent external ambient conditions can be taken into account in determining the intensity of the corrosive ambient atmosphere. A device installed close to the sea, for example, can be exposed to an increased salt or chloride concentration depending on the wind direction and/or wind speed.

Along with the geographical location, the geographical location data preferably also specify the degree of exposure to external climatic conditions, e.g. depending on whether an installation is located indoors or outdoors. In the case of installations inside plants, for example, an increased condensation risk can exist due to aggregation nuclei, such as dust.

Using the geographical location data, optionally operationally related day/night intervals, depending on the time of year, can also be taken into account in determining the intensity of the corrosive ambient atmosphere.

The advantages described above and below of the device disclosed here relate, optionally, to switch cabinets in electrical engineering, for example in industrial plant engineering, in which I/O components, such as e.g. measuring transducers or other types of electronic switching components, are arranged which communicate with field devices, sensors and actuators of an industrial plant. The disclosure similarly relates to a protective housing, optionally a switch cabinet, having the device described here for detecting the corrosive ambient atmosphere.

In a method for operating the device described above, the changes over time in at least two different ambient parameters, optionally air temperature and/or component temperature, air humidity and/or gas concentration are measured by means of internal sensors arranged inside the protective housing, wherein a sensor signal reflecting the respective change over time in the respective ambient parameter is generated. The sensor signals reflecting the respective changes over time in the ambient parameters are correlated with one another for the evaluation. The intensity of the corrosive ambient atmosphere is determined on the basis of deviations of the sensor signals, or of a parameter correlated therewith, from a reference value or reference value range taking into account the time duration and frequency of the deviations. An output signal reflecting the determined intensity of the corrosive ambient atmosphere is generated according to this result.

The advantages and the mode of operation of the method according to the disclosure can be derived directly from the description above and below relating to the device for detecting a corrosive ambient atmosphere.

Optionally, a time period indicating how often and how long the sensor signals deviate from a reference value or reference value range can be taken into account in the evaluation. In other words, the duration and frequency of contamination conducive to corrosion is taken into account in order to be able to predict possible damage due to corrosion.

Depending on the intensity of the corrosive ambient atmosphere, handling instructions, optionally, can be issued to a user by means of the output signal, or corresponding actuators are automatically activated in order to implement appropriate measures. An air conditioning system, ventilation or heating, for example, can be activated, optionally if the dew point is repeatedly or persistently understepped.

In a further example of the method according to the disclosure, at least one testpiece made from a test material can be arranged inside the protective housing in a learning phase and/or initialization phase, and at least one electrical characteristic of the testpiece can be measured under given ambient conditions over a predefined time period, wherein the test material is correlated with other materials installed in the protective housing and is taken into account in determining the intensity of the corrosive ambient atmosphere.

In one example of the method,

- an empirical database of metals typically installed in a switch cabinet is created;
- a correlation of material characteristics of these metals with those of the testpiece is determined; and
- the effect of the prevailing ambient conditions is determined as a function of time depending on temperature and relative air humidity, and also on gas concentration depending on the location (e.g. salt content in the air or close to the sea) and is taken into account in predicting corrosion-related failures before they occur. A correlation between the material characteristics of the test-piece and the other metals installed in the switch cabinet can be established, for example, by means of the electrochemical potential or on the basis of the Nernst equation.

BRIEF DESCRIPTION OF THE DRAWINGS

Further aspects and advantages of the disclosure will now be explained on the basis of an example shown in the drawings. The example should not be construed as a limiting example, but rather as one out of many possible ways to carry out the disclosure.

In the drawings.

DESCRIPTION

Figure 1:
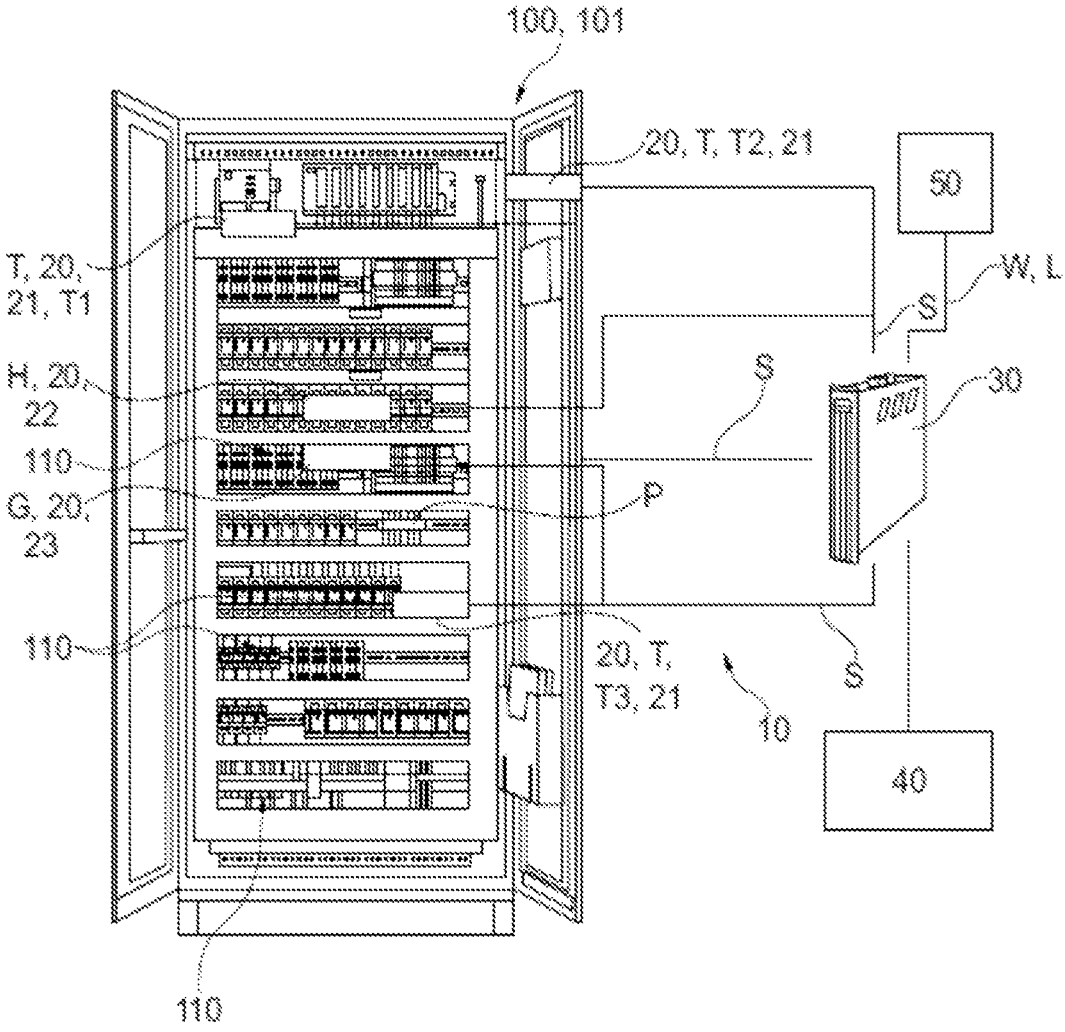
FIG. 1 shows a schematic representation of one possible exemplary embodiment of the device.

A first example of the device 10 for detecting a corrosive ambient atmosphere in a protective housing 100 which, in the example shown, is a switch cabinet 100, is explained with reference to FIG. 1. A multiplicity of I/O components 110 which have switching connections to field devices, sensors and actuators of an industrial plant are arranged in the switch cabinet 101.

The device 10 includes a plurality of internal sensors 20 which are designed to measure different ambient parameters T, H, G continuously or at recurring time intervals, and in each case to generate assigned sensor signals S which represent a change over time in the respective measured ambient parameter T, H, G.

The internal sensors 20 are connected via wired or wireless communications to an evaluation device 30 for evaluating the sensor signals S.

The sensor signals S can be, for example, digital or analog signals.

The evaluation device 30 can, for example, be a local evaluation device, wherein the evaluation device 30 can be arranged, optionally, inside the protective housing 100, or it can be an evaluation device of a data cloud in an intranet or the Internet.

In the example shown, three of the internal sensors 20 are designed as temperature sensors 21 and are arranged in different areas of the switch cabinet 101 in order to measure temperatures T. One of the temperature sensors 21 is configured to measure an air temperature T1, a further temperature sensor 21 is located in the area of a switch cabinet wall or door for the temperature measurement T2 of a cold spot. A temperature sensor 20 is arranged in the area of an I/O component 110 of the switch cabinet 101 in order to measure a component temperature T3.

The temperature sensors 21 are preferably designed as optical sensors, optionally as IR sensors.

The device 10 further includes an internal sensor 20 which is configured as an air humidity sensor 22 to measure the air humidity H inside the protective housing 100 or switch cabinet 101. An additional internal sensor 20 is designed as a gas sensor 23 to measure a concentration G of substances conducive to corrosion, such as, for example, a corrosive gas, optionally a halogenated compound, a gas containing chloride or hydrogen sulfide or a corresponding substance dissolved in water, contamination due to solid substances or substances dissolved in liquids.

The generated sensor signals S in each case represent the change over time in the measured ambient parameters T, H, G. The evaluation device 30 can be configured to receive the sensor signals S assigned to the ambient parameters T, H, G and to correlate them with one another in order to derive an intensity of the corrosive ambient atmosphere therefrom. Specifically, the intensity of the corrosive ambient atmosphere can be determined on the basis of deviations of the sensor signals S, or of a parameter correlated therewith, from a reference value or reference value range taking into account a time duration and a frequency of the deviations. An output device 40 can be configured to generate an output signal which reflects the determined intensity of the corrosive ambient atmosphere.

The output device 40 can be configured, for example, to output a warning signal if the intensity of the corrosive ambient atmosphere reaches a critical value. Generally speaking, the output signal can serve to indicate handling instructions to a user according to the determined intensity of the corrosive ambient atmosphere.

In other examples, actuators can be activated by means of the output signal to perform immediate actions. It is provided here, for example, to automatically activate a heating, a cooling, an air conditioning system and/or a filter system depending on the determined intensity of the corrosive ambient atmosphere.

For the evaluation, the evaluation device 30 can calculate a dew point as a correlated variable from the sensor signals S or data provided by the air humidity sensor 22 and by the temperature sensors 21. Deviations of the calculated dew point from a reference value or reference value range can indicate a condensation conducive to corrosion inside the switch cabinet 101. The intensity of the corrosive ambient atmosphere can be determined depending on the time duration and frequency of these deviations.

In order to determine the intensity of the corrosive ambient atmosphere, the evaluation device 30 can include, for example, a trained model, optionally a deep learning model, which has been trained in an initialization or learning phase to classify the intensity of the corrosive ambient atmosphere on the basis of the changes over time in the different ambient parameters T, H, G. The evaluation device 30 can be designed, for example, to determine the intensity of the corrosive ambient atmosphere, taking into account of a corrosion behavior of a corroding testpiece P empirically determined in advance, particularly in an initialization phase and/or in the learning phase.

The testpiece P consists, for example, of a base test material, optionally metal, of which the electrical characteristics, optionally conductivity, are empirically determined during the learning or during the initialization under the influence of corrosion. The testpiece P is typically mounted at an exposed location in the protective housing 100 or switch cabinet 101. The behavior of the testpiece P under the influence of corrosion can be correlated with other metals or materials installed in the protective housing 100, taking into account the electrochemical potential or the Nernst equation.

The evaluation device 30 can be further designed to receive local climate data W and/or local geographical location data L containing information relating to the local weather and/or the geographical location of the protective housing 100, and to take the data into account in determining the intensity of the corrosive ambient atmosphere. The evaluation device 30 can have, for example, a data connection to a weather station or to correspondingly designed external sensors 50 for this purpose. The weather data can contain, for example, information relating to an external temperature, wind speed, precipitation probability, etc., which can influence the corrosive ambient atmosphere prevailing in the protective housing 100. The device 10 can, for example, be subject to increased exposure due to corrosive gases, depending on the wind direction and its geographical location, particularly in relation to saltwater bodies or plant components of a chemical plant.

Figure 2:
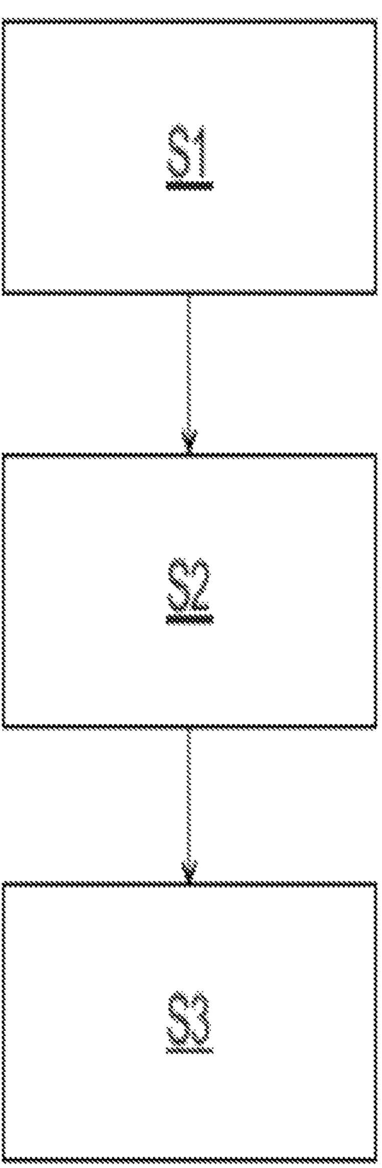
FIG. 2 is a block diagram which illustrates a method for operating the device shown in FIG. 1.

A method for operating the device 10 described above is schematically illustrated in the block diagram shown in FIG. 2. In the method for operating the device 10 described above, the changes over time in the different ambient parameters T, H, G, optionally air temperature and/or component temperature, air humidity and/or gas concentration, are measured in a first step S1 by the internal sensors 20, and a sensor signal S reflecting the respective change over time in the respective environment is generated. The sensor signals S reflecting the respective changes over time in the ambient parameters T, H, G are correlated with one another in a second step S2 for the evaluation, wherein the intensity of the corrosive ambient atmosphere is determined on the basis of deviations from a reference value or reference value range, taking into account the time duration and frequency of the deviations. An output signal reflecting the determined intensity of the corrosive ambient atmosphere is generated in a third step.

The testpiece P is arranged inside the protective housing 100 in a learning phase or initialization phase in order to train or initialize the device 10. During the learning phase or initialization phase, an electrical characteristic of the testpiece, optionally its electrical conductivity, is measured over a predefined time period under given corrosive ambient conditions in order to determine the effect of corrosion on the test material. This empirically determined corrosion behavior of the testpiece P is correlated with other materials installed in the protective housing and is taken into account accordingly in determining the intensity of the corrosive ambient atmosphere. In a further development, it is provided to create an empirical database of metals typically installed in a switch cabinet and to determine correlations between material characteristics of these metals and those of the testpiece by means of the electrochemical potential or on the basis of the Nernst equation. The effect of the ambient conditions prevailing during operation is determined by sensors as a function of time depending on the measured temperature T, air humidity H and/or gas concentration G, and is taken into account in predicting the corrosive ambient atmosphere.

In summary, according to the disclosure not only limit values can be used, but also the temporal aspect of changing ambient conditions in order to determine the intensity of the corrosive ambient atmosphere can be taken into account. The evaluation of the sensor signals can take into account the duration and frequency of measured contamination in order to obtain meaningful information relating to the occurrence of an atmosphere conducive to corrosion and to reliably determine the intensity of the corrosive ambient atmosphere.

REFERENCE SYMBOL LIST

10 Device
20 Internal sensor
21 Temperature sensor
22 Air humidity sensor
23 Gas sensor
30 Evaluation device
40 Output device
100 Protective housing
101 Switch cabinet
110 I/O component
T Ambient parameter, temperature
H Ambient parameter, air humidity
G Ambient parameter, gas concentration
S Sensor signal
T1 Temperature
T2 Temperature
T3 Temperature
P Testpiece
W Local climate data
L Geographical location

What is claimed is:

1. Device for determining an intensity of a corrosive ambient atmosphere in a protective housing, comprising:
at least two internal sensors designed to detect changes over time in predefined different ambient parameters inside the protective housing, and to generate sensor signals reflecting the respective changes over time in the predefined different ambient parameters;
an evaluation device designed to receive the sensor signals and to evaluate the sensor signals in correlation with one another in order to determine the intensity of the corrosive ambient atmosphere on basis of deviations of the sensor signals, or of a parameter correlated with the sensor signals, from a reference value or reference value range, taking into account a time duration and/or frequency of the deviations; and
an output device designed to generate an output signal reflecting the determined intensity of the corrosive ambient atmosphere
wherein the evaluation device is designed to determine the intensity of the corrosive ambient atmosphere, taking into account a corrosion behavior of a corroding testpiece empirically determined in advance.

2. Device according to claim 1,
wherein
the protective housing is a switch cabinet.

3. Device according to claim 1,
wherein
the ambient parameters include an air temperature, a component temperature, an air humidity, and/or a gas concentration.

4. Device according to claim 1,
wherein
the evaluation device comprises a trained model which is implemented in hard- and/or software and is trained in a learning phase to classify the intensity of the corrosive ambient atmosphere on the basis of the changes over time in the different ambient parameters.

5. Device according to claim 4,
wherein
the trained model is a deep learning model.

6. Device according to claim 1,
wherein
at least one of the internal sensors is an air humidity sensor, and at least one further of the internal sensors is a temperature sensor, the air humidity sensor and the temperature sensor are designed to generate the sensor signals reflecting the changes over time in the different ambient parameters, respectively, and the evaluation device is designed to determine the intensity of the corrosive ambient atmosphere taking into account a dew point calculated on basis of the sensor signals of the air humidity sensor and of the temperature sensor.

7. Device according to claim 6, wherein the temperature sensor is designed to measure a temperature of a cold spot inside the protective housing, wherein the temperature sensor defines an essentially isolated measuring point at the cold spot or is designed as a surface temperature sensor.

8. Device according to claim 6, wherein the temperature sensor is an optical sensor.

9. Device according to claim 8, wherein the optical sensor is an IR sensor.

10. Device according to claim 1, wherein at least one of the internal sensors is designed to measure a gas concentration of a corrosive gas inside the protective housing.

11. Device according to claim 1, wherein at least one of the internal sensors is designed to measure a chloride concentration and/or hydrogen sulfide concentration inside the protective housing.

12. Device according to claim 1, wherein the evaluation device is designed to receive local climate data and/or geographical location data which contain information dependent on a geographical location of the protective housing, and to take the data into account in determining the intensity of the corrosive ambient atmosphere.

13. Method for determining an intensity of a corrosive ambient atmosphere in a protective housing, comprising:

measuring, by internal sensors arranged inside the protective housing, changes over time in at least two different ambient parameters and generating sensor signals reflecting the changes over time in the at least two different ambient parameters;

correlating the sensor signals reflecting the changes over time in the at least two different ambient parameters with one another;

determining the intensity of the corrosive ambient atmosphere on basis of deviations of the sensor signals, or of a parameter correlated with the deviation of the sensor signals, from a reference value or reference value range taking into account a time duration and frequency of the deviations;

generating an output signal reflecting the determined intensity of the corrosive ambient atmosphere;

measuring at least one electrical characteristic of at least one testpiece under given ambient conditions over a predefined time period, the testpiece being made from a test material and being arranged inside the protective housing in a learning phase and/or initialization phase; and correlating the test material with other materials installed in the protective housing;

wherein a change in the at least one electrical characteristic of the testpiece and the other materials correlated therewith is taken into account in determining the intensity of the corrosive ambient atmosphere.

14. Method according to claim 13, wherein the at least two ambient parameters include an air temperature, a component temperature, an air humidity, and/or a gas concentration.

* * * * *